US012776398B2

(12) United States Patent
Schlegel et al.

(10) Patent No.: US 12,776,398 B2
(45) Date of Patent: *Oct. 27, 2026

(54) SYSTEM FOR MANAGEMENT AND IMPROVEMENT OF RESPONSE TO INDIVIDUAL MEDICAL EVENTS

(71) Applicant: BeEnabled, LLC, Coshocton, OH (US)

(72) Inventors: Jennifer Grace Schlegel, Columbus, OH (US); Anders Ian Sondergaard, Beavercreek, OH (US)

(73) Assignee: BeEnabled, LLC, Coshocton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/795,839

(22) Filed: Aug. 6, 2024

(65) Prior Publication Data

US 2024/0395378 A1 Nov. 28, 2024

Related U.S. Application Data

(63) Continuation of application No. 17/209,461, filed on Mar. 23, 2021, now Pat. No. 12,080,390.

(60) Provisional application No. 62/993,588, filed on Mar. 23, 2020.

(51) Int. Cl.
*G16H 10/60* (2018.01)

(52) U.S. Cl.
CPC .................................. *G16H 10/60* (2018.01)

(58) Field of Classification Search
CPC ................................ G16H 10/60; G06F 3/167
See application file for complete search history.

(56) References Cited

U.S. PATENT DOCUMENTS

2010/0016746 A1* 1/2010 Hampton ............... A61B 5/747 600/523
2012/0218102 A1 8/2012 Bivens et al.
2016/0135706 A1 5/2016 Sullivan et al.
2017/0182329 A1 6/2017 Sullivan et al.
2018/0198906 A1 7/2018 Gabel
(Continued)

FOREIGN PATENT DOCUMENTS

WO 2004057853 A2 7/2004

OTHER PUBLICATIONS

International Searching Authority, International Search Report and Written Opinion, mailed Jun. 7, 2021, issued in connection with International Patent Application No. PCT/US2021/023623, 9 pages.

*Primary Examiner* — Shahid Merchant
*Assistant Examiner* — David Choi
(74) *Attorney, Agent, or Firm* — McDonnell Boehnen Hulbert & Berghoff LLP

(57) ABSTRACT

Computer-implemented method and system for improving response to medical events and bystander assistance in said medical situations. The method and system provide an interface between the person experiencing a health related event, i.e. the "user," and someone around said person witnessing the health related event, i.e. the "bystander." On a mobile device, the method comprises alerting a bystander to the user and the medical event they are experiencing. Providing the bystander with relevant information through an interaction between the user mobile device and bystander mobile device via a series of sequential questions and commands; therefore, letting the bystander know the type of attention the situation merits.

18 Claims, 7 Drawing Sheets

(56) References Cited

U.S. PATENT DOCUMENTS

| | | | | |
|---|---|---|---|---|
| 2018/0221645 | A1* | 8/2018 | Medema ................. | H04W 4/02 |
| 2019/0043615 | A1 | 2/2019 | Subbarao et al. | |
| 2019/0216350 | A1 | 7/2019 | Sullivan et al. | |
| 2019/0279327 | A1 | 9/2019 | Braun et al. | |
| 2021/0006961 | A1 | 1/2021 | King-Berkman et al. | |

* cited by examiner

SYSTEM FOR MANAGEMENT AND IMPROVEMENT OF RESPONSE TO INDIVIDUAL MEDICAL EVENTS

CROSS-REFERENCE TO RELATED APPLICATION

The present application is a continuation of U.S. patent application Ser. No. 17/209,461, filed Mar. 23, 2021, which claims priority to U.S. Provisional Patent Application No. 62/993,588, filed Mar. 23, 2020, the contents of both of which are herewith incorporated by reference.

Public emergency systems, such as the 9-1-1 Emergency System in the United States, are an invaluable tool for the management of many types of emergencies, including medical events. However, the improper use of public emergency systems have had negative effects on the economy and society. Furthermore, unnecessary calls to public emergency systems for non-life threatening emergencies may result on an economic burden on the person suffering the non-life threatening medical event. Moreover, unnecessary calls to public emergency systems affect hospital resources and paramedic resources that would be better spent on critical emergencies.

It is estimated that fifty nine percent (59%) of the adult population in the United States have a chronic illness. Thirty percent (30%) of all emergency room visits for the chronic illness population are for reasons that are both non-life threatening; thus, they are deemed unnecessary. Similarly, a large percentage of emergency room visits involving individuals suffering from mental health conditions and geriatric individuals are also deemed non-life threatening and avoidable.

Moreover, the lack of knowledge regarding relevant health information from an individual experiencing a medical episode may affect the public emergency system's efficiency. Current methods for sharing health information, such as medical ID bracelets and medical identification on smart devices, can go unnoticed or even misinterpreted by the people assisting said individuals.

In view of the above, there is a need for a system and method to reduce the number of unnecessary calls to public emergency systems for non-life threatening situations while also providing relevant health information to assist in said situation and empowering the affected person to regain control of their choice in medical treatment.

Currently disclosed is a computer-implemented system and method to improve how public emergency systems are used on behalf of people experiencing medical events. Said system and method also improves the public emergency system's efficiency as it provides for the quick delivery of relevant medical information relating to the person experiencing the medical event to bystanders assisting said person. Additionally, the currently disclosed system and method also improves public emergency system's efficiency by providing, in life-threatening situations, relevant medical history information relating to the person experiencing the medical event. By providing a way to quickly share relevant information about existing health conditions with bystanders and paramedics, the disclosed system and method allows for the reduction of expenses related to medical events and improve emergency response.

Currently disclosed is a computer-implemented method for improving response to medical events, comprising: at a user mobile device, and in response to receiving a request: activating a preset timer, wherein completion of the preset timer causes the user mobile device to gather at least one alert parameter; displaying the at least one alert parameter on the user mobile device, wherein the at least one alert parameter alerts a bystander of a potential medical event and instructs to approach the user mobile device; displaying a readable code on the user mobile device; displaying instructions to scan the readable code with bystander mobile device, wherein scanning the readable code causes the bystander mobile device to connect to a server via a network. Further, the method comprises transmitting data from the server to the bystander mobile device, wherein the data is stored in a database of the server, wherein the data correspond to at least one action of a set of actions to be carried out on the bystander mobile device. Moreover, the method comprises displaying information corresponding to the at least one action of the set of actions on the bystander mobile device, wherein the information involves a question or command, wherein responding to the at least one action of the set of actions causes the bystander mobile device to connect to the server and for the server to transmit further data to the bystander mobile device, wherein said further data is dependent on the response to the at least one action of the set of actions.

Also disclosed is a system configured to improving response to medical events, the system comprising a user mobile device comprising: a processor; and a memory configured to store instructions that, when executed by the processor, causes the system to carry out steps that include: receiving a request: in response to the request, activating a preset timer, wherein completion of the preset timer causes the user mobile device to gather at least one alert parameter. Further, the system comprises displaying the at least one alert parameter on the user mobile device, wherein the at least one alert parameter alerts a bystander of a potential medical event and instructs to approach the user mobile device; displaying readable code on the user mobile device; displaying instructions to scan the readable code with bystander mobile device, wherein scanning the readable code causes the bystander mobile device to connect to a server via a network. Moreover, the system comprises transmitting data from the server to the bystander mobile device, wherein the data is stored in a database of the server, wherein the data correspond to at least one action of a set of actions to be carried out on the bystander mobile device; and displaying the at least one action of the set of actions on the bystander mobile device, wherein each action of the set of actions involves a question or command, wherein responding to the at least one action of the set of actions causes the bystander mobile device to connect to the server and for the server to transmit further data to the bystander mobile device, wherein said further data is dependent on the response to the at least one action of the set of actions.

In either method or system, alternatively or additionally, wherein the bystander mobile device is in close proximity to the user mobile device, the user mobile device transmits a notification to the bystander mobile device. Acceptance of notification by the bystander mobile device causes the bystander mobile device to connect to a server via a network.

In either method or system, the preset timer may be manually activated. Alternatively, or additionally, the user mobile device may automatically activate the preset timer when unusual activity of a tracked or measured biometric is detected.

Further, upon completion of the preset timer, the user mobile device may gather at least one alert parameter, said at least one alert parameter may comprise a prerecorded audio message, a vibration alert, a visual display of lights, or a combination of these. Displaying the at least one alert parameter on the user mobile device serves to alert a bystander that the user of the mobile device is experiencing a medical event and may need assistance. Moreover, upon completion of the preset timer, the user mobile device may gather a second alert parameter, said second alert parameter comprising geographical location coordinates of the user mobile device. The user mobile device records said geographical location coordinates and sends the same to the server, causing the server to transmit the geographical location of the user mobile device to another mobile device.

In either method or system, the data stored in the database of the server comprises information relating to the user's medical condition or conditions.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION OF THE DRAWINGS

Figure 1:
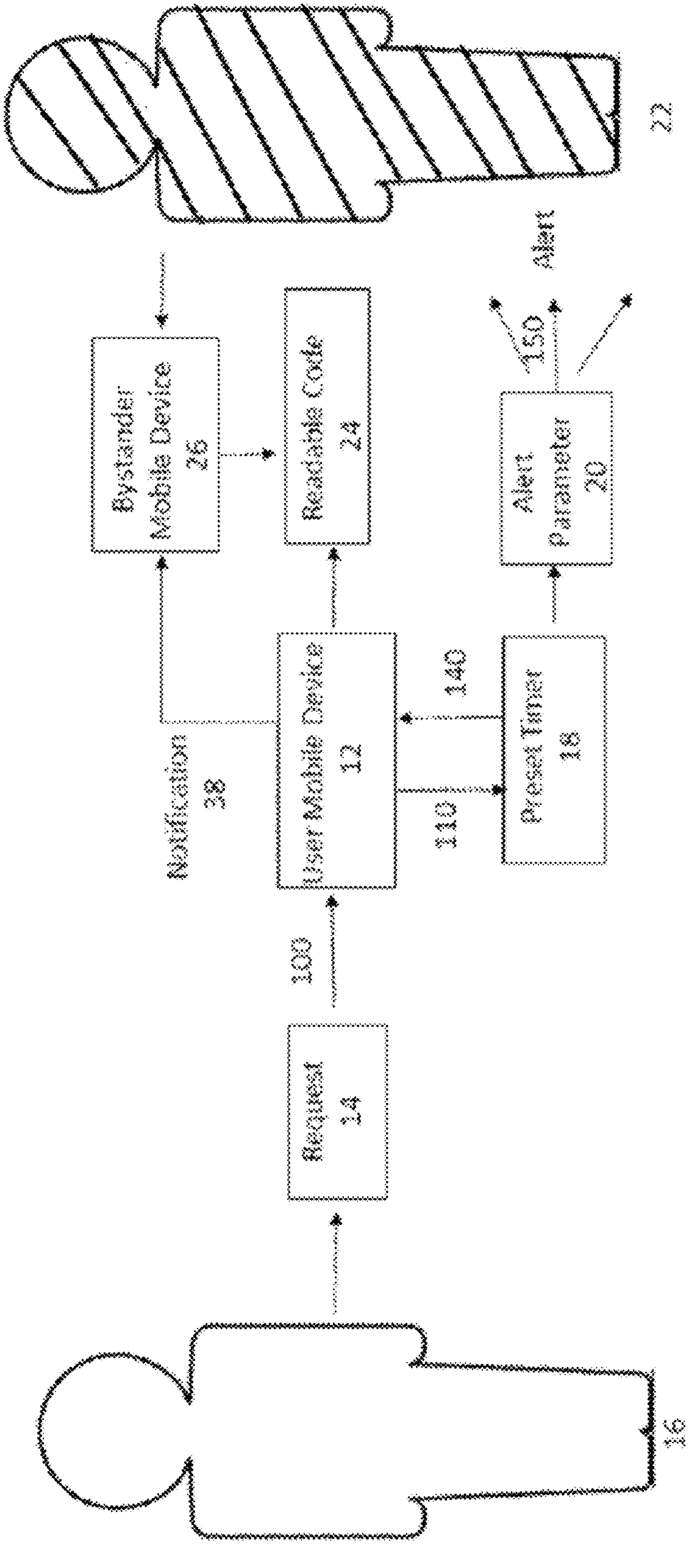
FIG. 1 illustrates a diagram of the currently claimed system.

When a bystander notices a person experiencing a medical event, regardless if said medical event warrants it or not, the typical reaction of the bystander is to call a public emergency system, for example, the 9-1-1 Emergency System in the United States. Said immediate response to call a public emergency system may result in a large number of unnecessary calls to the public emergency system, which in turn, may result in unnecessary expenses for the person experiencing the medical event. Currently disclosed is a system and method that provides a way to reduce the number of unnecessary calls to public emergency systems while also improving a way of sharing relevant information and giving back autonomy to the patient on how their medical health event is handled.

As illustrated in FIGS. 1-7, the currently disclosed computer-implemented method and system improves response to medical events. The system and method provides an interface between a person experiencing a health related event, i.e. the "user," and someone around said person witnessing the health related event, i.e. the "bystander." When a user experiences a medical event, the system alerts a bystander to the situation. The system provides the bystander with information relevant to the user's medical condition and to the medical event the user is currently experiencing. The system provides the bystander with the user's exact needs and provides them with tools to evaluate the medical situation through a series of yes/no questions customized to the user, which may help the bystander to determine the type of attention the situation merits, e.g. call emergency contact, call user's physician, or call public emergency system, if needed.

As shown in FIGS. 1-7, the currently disclosed system 15 is used with a user mobile device 12, said user mobile device comprising a processor and a memory. The user mobile device 12 may be a smartphone, tablet, or smart wearable. A smart wearable includes a smartwatch, wristband, neckpiece, armband, keychain, shoe, glove, pin, etc. A request 14 is sent to the user mobile device 12 to trigger the system 15. The system is triggered (100) by the user 16 of the user mobile device 12 manually sending a request 14 to the user mobile device 12 when the user 16 experiences or believes they will experience a medical event, for example, a seizure, panic attack, severe allergic reaction, or diabetic flare up. Alternatively, or in addition, the system may be automatically triggered when the user mobile device 12 detects an unusual activity in a measured biometric indicator, for example, unusual heartbeat, blood sugar level, or blood pressure.

Figure 3:
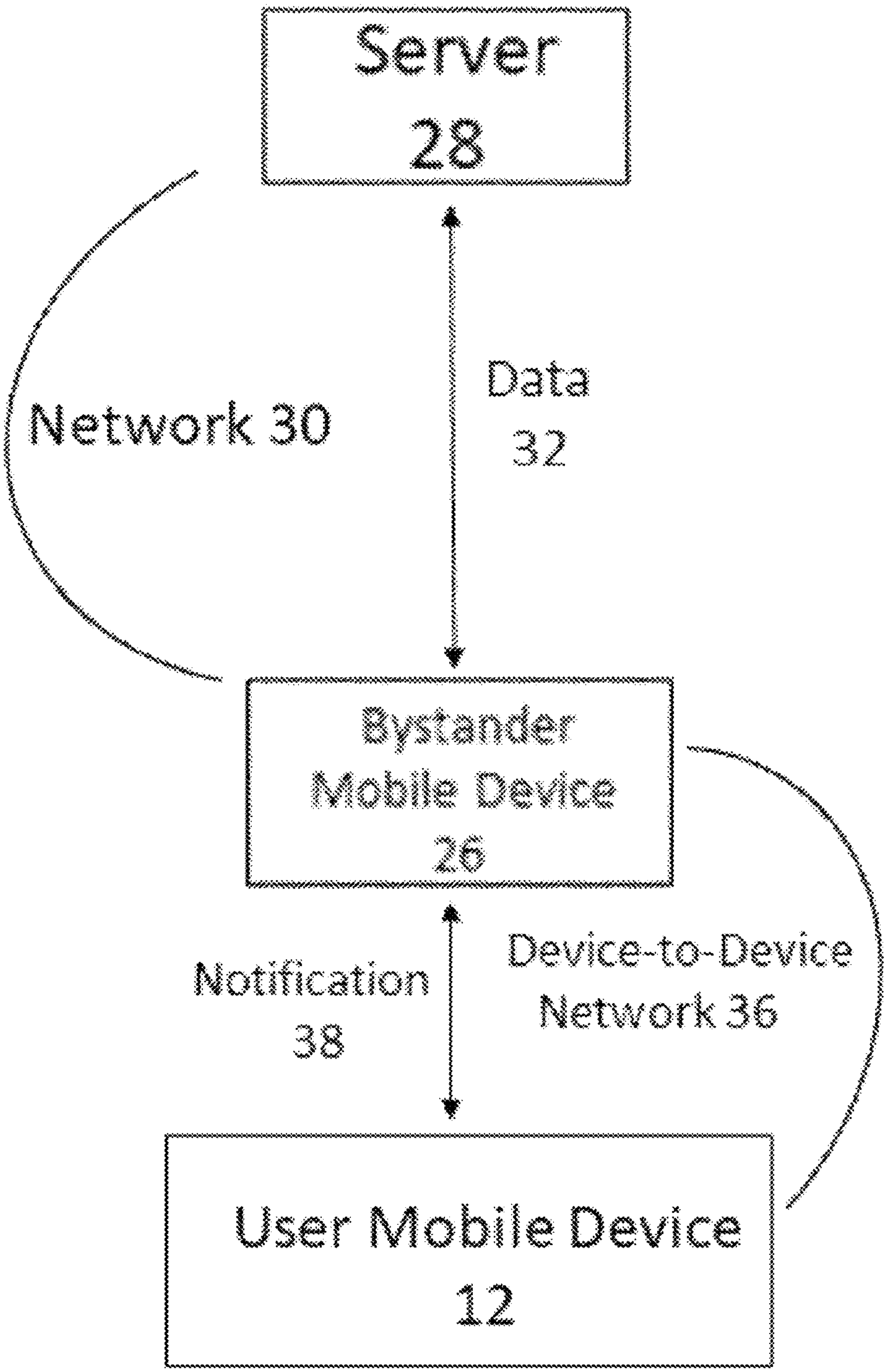
FIG. 3 illustrates a diagram of the currently claimed system.
Figure 4:
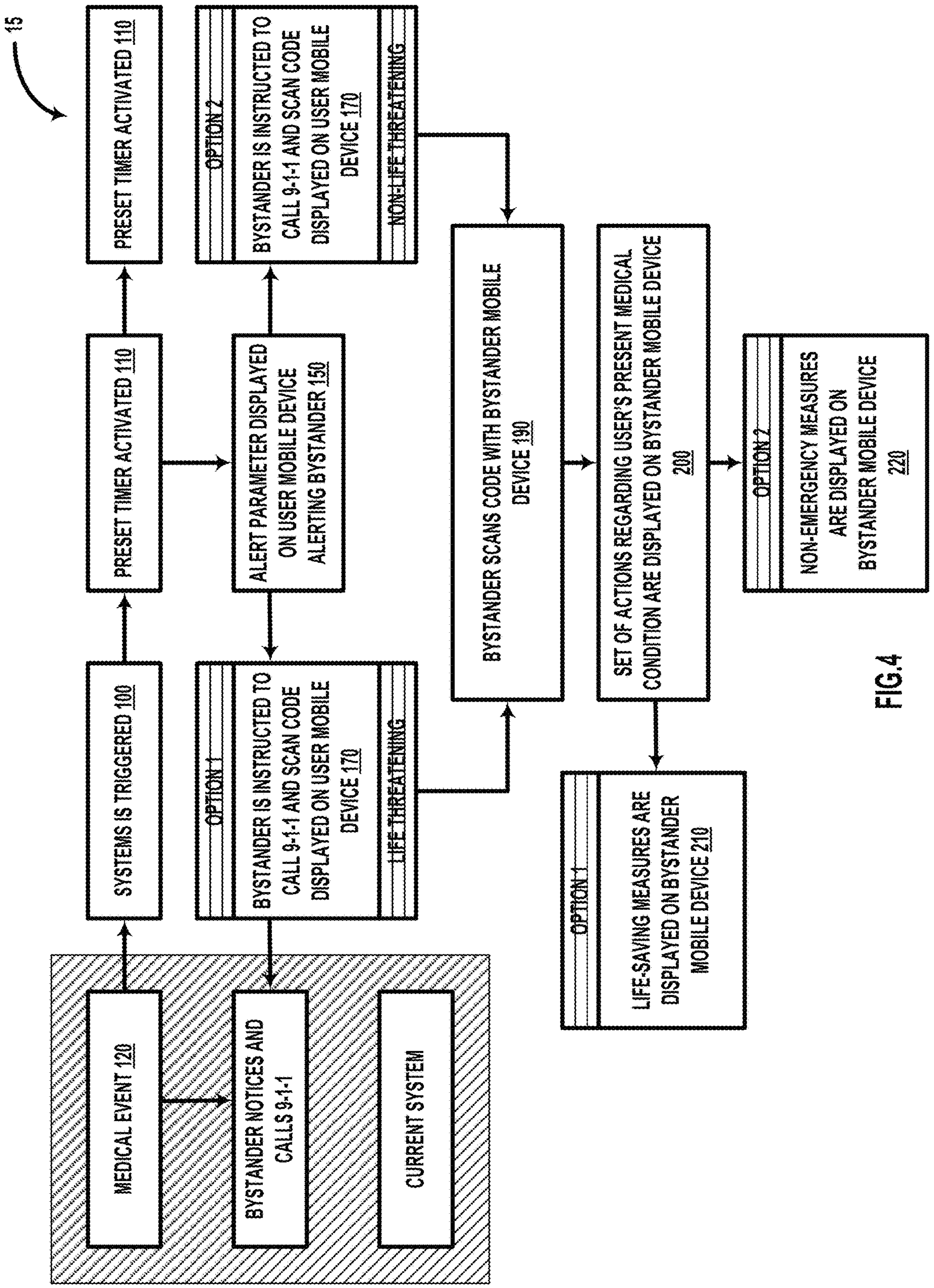
FIG. 4 illustrates a flowchart of the currently claimed system.

Once the system is triggered (100), a preset timer 18 is activated (110) on the user mobile device 12. If the system was activated by accident, the user of the user mobile device may manually disable the preset timer (130), which in turn deactivates the system. On the other hand, upon completion of the preset timer (140), the user mobile device 12 gathers at least one alert parameter 20 and said at least one alert parameter is displayed on the user mobile device (150). The at least one alert parameter 20 comprises an alert, either visual, audible and/or both, to draw the attention of a bystander 22 to a medical event (120) being experienced by the user 16. The at least one alert parameter 20 may include a recorded audio message, visual display of light (e.g. flashing lights), and/or vibration. The flashing lights alert may include different light patterns and colors. The vibration alert may include different vibration patterns. The at least one alert parameter 20 alerts to the user's medical event 120 and instructs to approach the user mobile device. As shown in FIG. 3 as "Option 1," if the medical event is a life-threatening event, for example, an anaphylactic shock or diabetic flare-up, the system directs the bystander to call the public emergency system, such as 9-1-1 Emergency System (170). On the other hand, if the medical event is a non-life threatening event that does not require an emergency room visit ("Option 2"), for example, some seizures or panic attacks, the system will request the bystander not to call public emergency system immediately (180).

Figure 2:
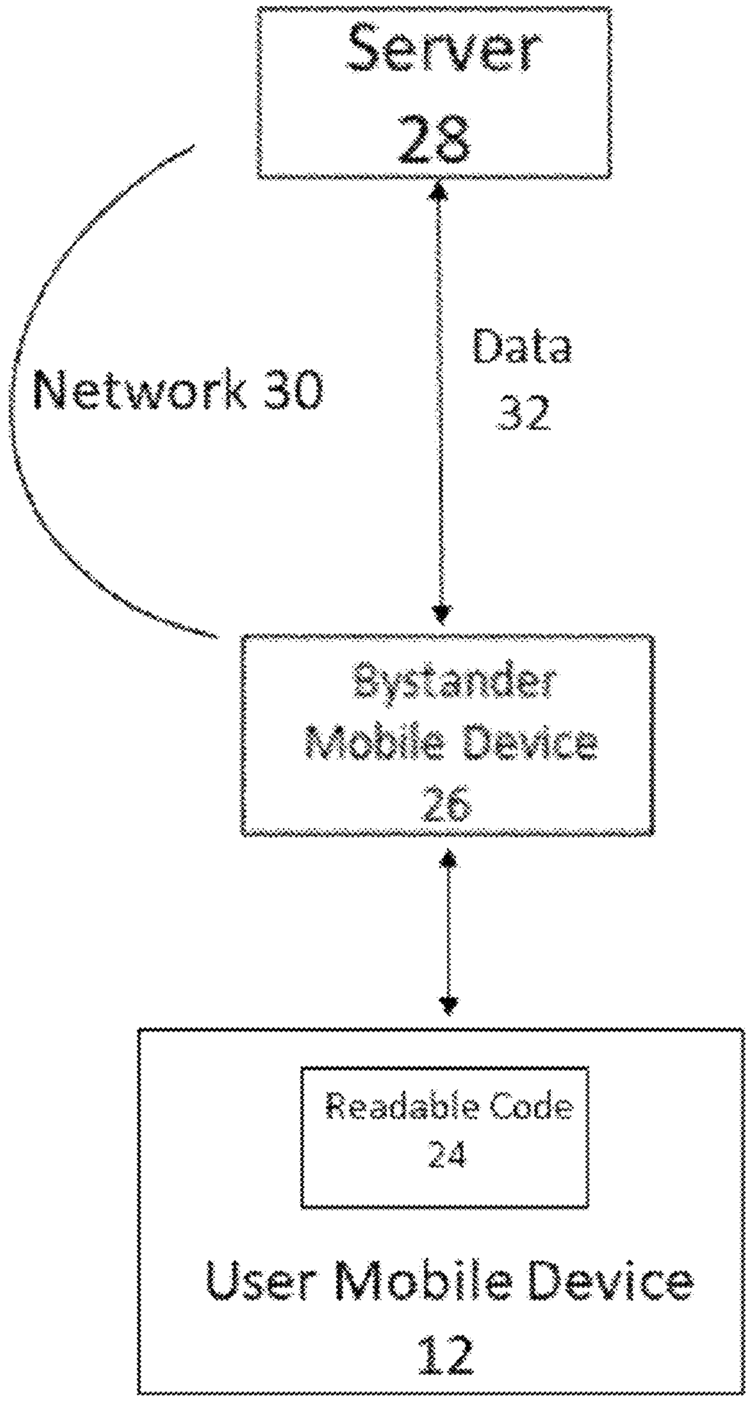
FIG. 2 illustrates a diagram of the currently claimed system.

As shown in FIGS. 2-3, in either of the above-identified situations, the user mobile device 12 displays a message and a readable code 24. The message instructs to scan the readable code 24 displayed on the user mobile device 12 with the bystander mobile device 26. The readable code may include a QR code, a barcode, etc. For example, the readable code may be scanned with the bystander mobile device's camera; thus, eliminating the necessity of searching through the user's belongings or persona for a medical ID or health information. Alternatively, or additionally, the user mobile device 12 may transmit a notification 38 to the bystander mobile device 26 via a device-to-device network 36. Said device-to-device network may include Bluetooth technology or any technology that allows wireless data transfer or exchange between mobile devices over short distance.

Once the readable code is scanned with the bystander mobile device (190), or the bystander mobile device accepts the notification transmitted from the user mobile device, the bystander mobile device 26 connects to a server 28 via a network 30.

The server then sends data 32 stored in the database of the server to the bystander mobile device 26. Said database comprises information relating to the user and the user's medical conditions. The data 32 sent to the bystander mobile device comprises at least one action of a set of actions 34 to be carried out on the bystander mobile device 26. Information corresponding to the at least one action of the set of actions is displayed on the bystander mobile device. The bystander is then instructed to answer the set of actions (200). Once a response to at least one action of the set of actions is entered, the bystander mobile device sends the response to the server and the server then transmits further data back to the bystander mobile device. This further data corresponds to other actions of the set of actions, e.g. questions or commands relating to the user medical condition(s) and steps to follow. The further data will depend on the response to the at least one action of the set of actions.

Figure 6:
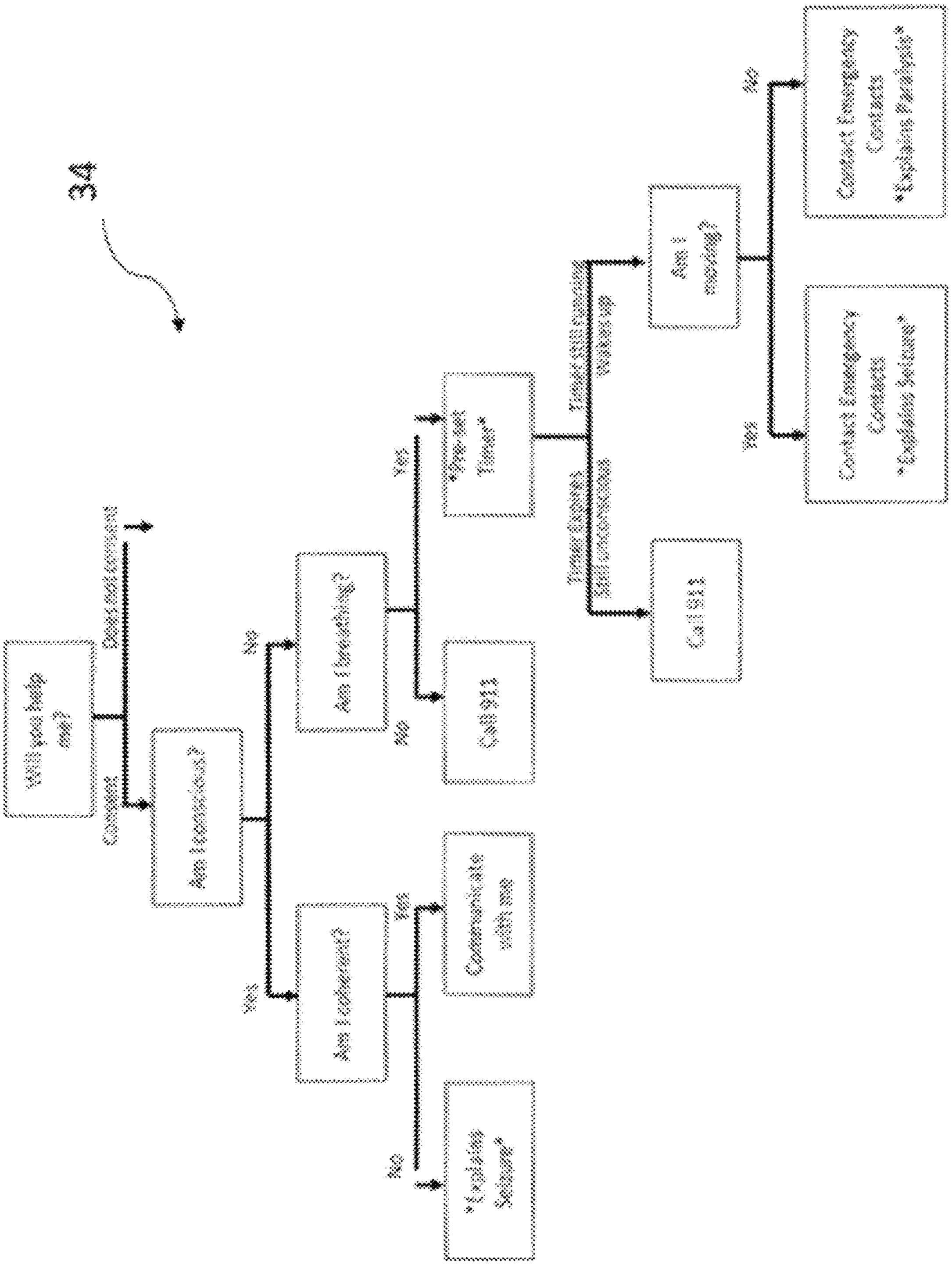
FIG. 6 illustrates a flowchart of an example of the set of actions of the currently claimed system.
Figure 7:
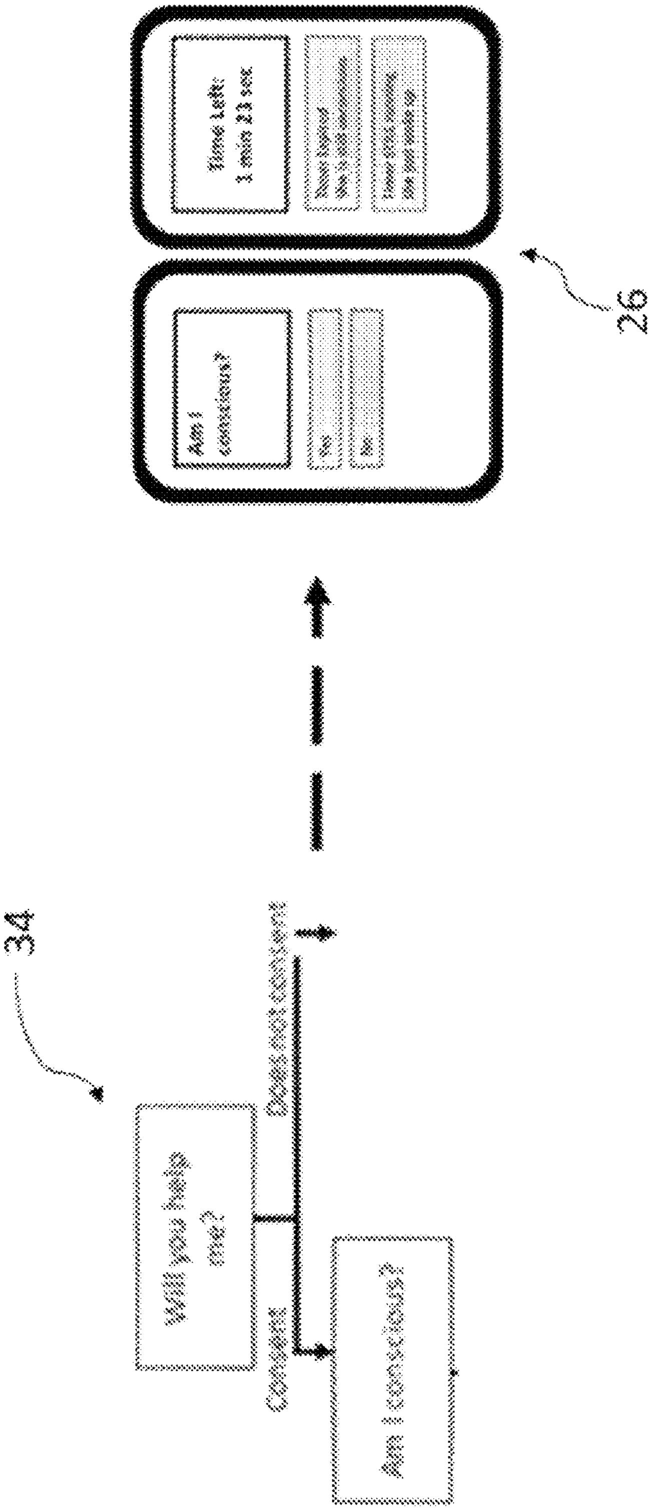
FIG. 7 illustrates a flowchart of an example of the set of actions of the currently claimed system.

FIGS. 6-7 show examples of the set of actions 34. The set of actions comprises a set of questions or commands. Said questions or commands may be in the form of a questionnaire that has been tailored to the user. The questions or commands allow for the quick assessment of the medical event. It also helps to narrow down the appropriate course of action in the particular situation. In that sense, the system may provide for minimal bystander's assistance, including messaging user's caretakers for assistance, helping user into a more comfortable position, or accessing devices and equipment in the user's possession (for example, an inhaler). The type of assistance required would be determined by the answers to the user's personalized questionnaire. For example, if based on the responses entered, it is determined the medical event involves a non-life threatening event, then the set of actions may include non-emergency measures that could be taken. If based on the responses entered, it is determined the medical event involves a life-threatening event, then the set of actions may include life-saving measures will also including instructions to call public emergency system.

The system provides the bystander with specific and relevant user's health information. In life-threatening situations, the bystander can use this information to improve the assistance they can provide to the user. The information could also be shared with the public emergency system's call coordinator and paramedics to improve the emergency response. In cases where the condition is not life-threatening, the bystander receives user-personalized instructions on the appropriate actions to take and additional preconfigured resources to contact, such as emergency contacts or personal physicians. Through these steps, the bystander quickly receives relevant information and user-personalized directions that could not be easily shared through other currently available products.

Figure 5:
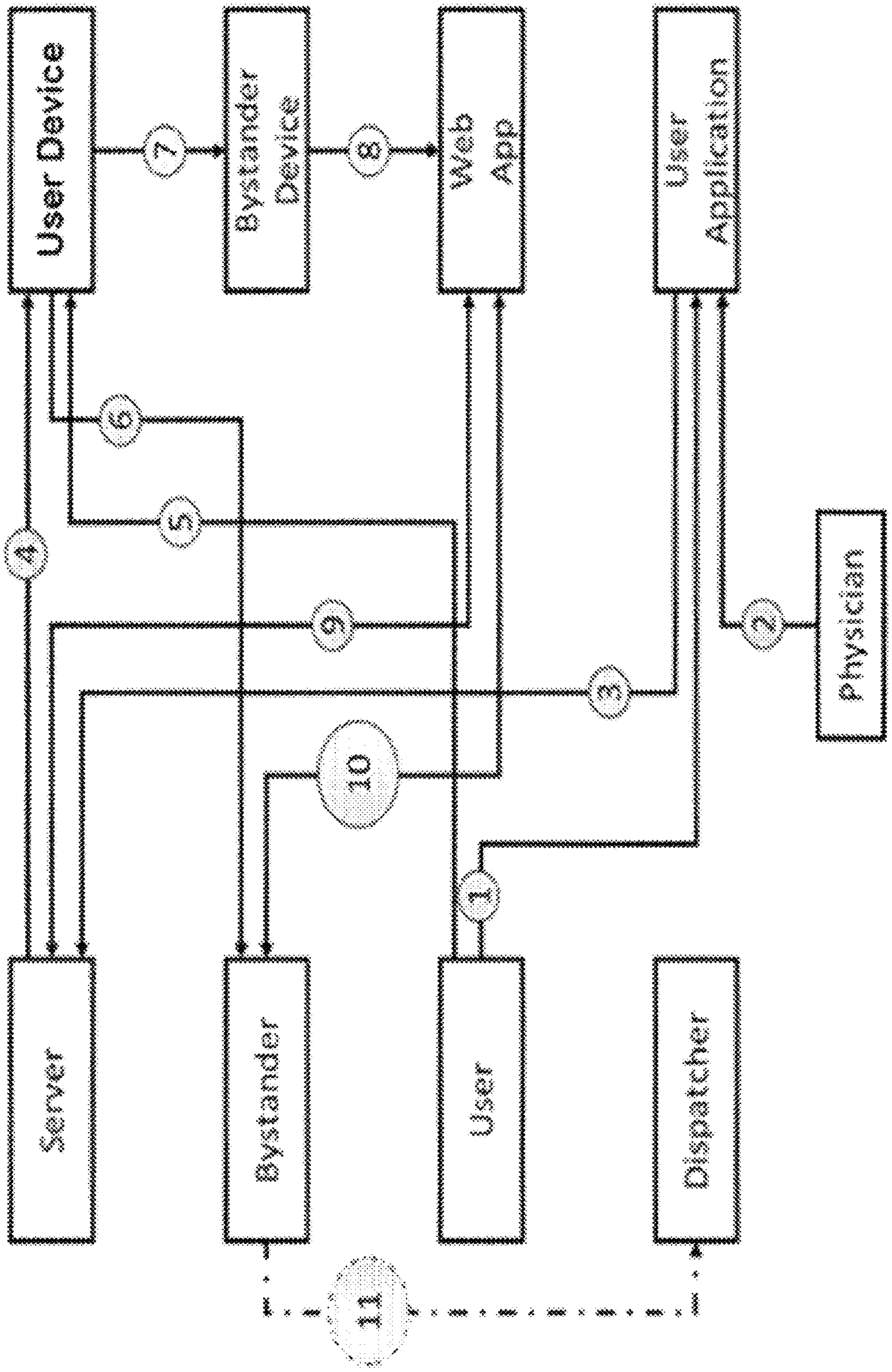
FIG. 5 illustrates a flowchart of the currently claimed system.

As illustrated in FIG. 5, the user may input their personal information into a user application (1). Alternatively, or additionally, the user's physician may input information relevant to the user's health into the user application (2). The information includes customizable information. The user may input information and set parameters to follow regarding, for example, length of the preset timer, or action or option to follow according to visible symptoms.

The user application is uploaded into the server (3) to be stored in the server's database. Then, the server downloads (4) relevant parts of the user's application to the user mobile device, including, for example, a readable code.

When the user of the user mobile device is experiencing a medical event, the user mobile device receives a request, triggering the system (5). The user may manually trigger the system on the user mobile device. Alternatively, or additionally, the system may be automatically activated on the user mobile device when the user mobile device detects an unusual change in a measured biometric indicator.

Triggering the system results in the activation of a preset timer. Once the preset timer runs its time, the user mobile device gathers at least one alert parameter and displays the same on the user mobile device. The at least one alert parameter alerts any bystander near the user to the fact that the user is experiencing a medical event (6). The at least one alert parameter may be an attention grabbing signal, for example, an audio message, flashing lights, vibration, and/or combination of these.

Alternatively, or additionally, upon completion of the preset timer, the user mobile device may gather a second alert parameter. The second alert parameter may include the user mobile device geographic location coordinates (e.g. latitude, longitude, altitude), which can identify the current location of the user mobile device. The second alert parameter may also include recorded information of the medical event being experienced by the user of the mobile device. For example, the second alert parameter may include activation time of the system, detected change in monitored biometric, etc. Then, the user mobile device transmits the recorded information to the server. Upon receipt of said information, the server may transmit the same to another mobile device, wherein the another mobile device is mobile device belonging to a preselected emergency contact of the user of the user mobile device. The server may transmit the information to the another mobile device in the form of a text, call or email. Further, the server may transmit the collected and recorded information to a third party application, for example, a group messaging application.

Once the preset timer is activated and completed, the at least one alert parameter instructs the bystander to approach the user mobile device. The user mobile device then displays a readable code and instructions for the bystander to scan the code with their mobile device (7). Alternatively, or additionally, the user mobile device may transmit a notification to the bystander mobile device. Alternatively, or additionally, the user mobile device may display information notifying the bystander that the user is experiencing a medical event. Thus, even if the bystander does not have a mobile device to scan the readable code, the bystander can still assist the user.

Once the bystander mobile device scans the readable code and/or accepts the notification sent by the user mobile device, the system directs the bystander mobile device to a web-based application with the user's medical information and personalized questionnaire (8). Scanning the readable code or accepting the notification causes the bystander mobile device to connect to a server. The server then transmits to the bystander mobile device information relating to the user's medical condition (9). This information is provided as a set of actions to be taken on the bystander mobile device (10). The set of actions involve a set of questions or commands specifically relating to the user medical condition.

The set of actions may further involve accessing third party applications (11). Once the bystander enters a response to at least one action of the set of actions on the bystander mobile device, the entered response is transmitted from the bystander mobile device to the server. Then, the server sends data corresponding to further action to be taken on the bystander mobile device. The further action may involve accessing third party applications, such as an emergency system, informational videos, messaging platforms, telehealth support platforms, etc.

Alternatively, or additionally, once a response to at least one action of the set of actions is entered in the bystander mobile device, said response is transmitted from the bystander mobile device to the server, wherein the response is recorded. Then, the recorded response is transmitted to the user mobile device. Further, the response may be then displayed on the user mobile device. For example, the user mobile device may display a message stating the bystander has accepted to assist the user. Further, the user mobile device may display specific responses to the set of actions entered on the bystander mobile device.

Alternatively, or additionally, once a response to at least one action of the set of actions is entered on the bystander mobile device, said response is transmitted from the bystander mobile device to the server, then the server sends a command to the user mobile device causing the user mobile device to play a soothing action. Said soothing action may include playing music, videos, photos, specific vibration pattern, etc.

Alternatively, or additionally, once a response to at least one action of the set of actions is entered on the bystander mobile device, said response is transmitted from the bystander mobile device to a second server. The second server then transmits the response to emergency response personnel's computer device. Information transmitted to emergency response personnel's computer device may include user's current medical condition, emergency contact information, and current medications, among other things.

As explained and shown in FIGS. 1-7, the currently disclosed system provides for the improvement of bystander assistance in medical situations. It further provides an alternative option for bystanders to handle health events, empowering the user experiencing the medical event to regain control of their choice in treatment.

While this invention has been shown and described with respect to a detailed embodiment thereof, it will be understood by those skilled in the art that changes in form and detail thereof may be made without departing from the scope of the claims of the invention.

What is claimed is:

1. A computer-implemented method for improving response to medical events, comprising:

in response to a manual user activation or an automatic user activation, activating a preset timer by a user mobile device;

in response to completion of the preset timer, causing the user mobile device to transmit a notification to a bystander mobile device so as to alert a bystander that a user of the user mobile device is experiencing a medical event and that the user may need assistance;

in response to an acceptance of the notification by way of the bystander mobile device, causing the bystander mobile device to connect to a server via a network;

upon connecting the bystander mobile device to the server, transmitting data from the server to the bystander mobile device, wherein the data comprises:

information indicative of a medical condition of the user and the medical event that the user is experiencing; and at least one action of a set of actions to be carried out on the bystander mobile device, wherein the set of actions comprises a series of actions that are customized to the user's medical condition and the medical event; and displaying, on the bystander mobile device, information corresponding to the at least one action of the set of actions, wherein the information involves a question or command to help the bystander evaluate or assist with the medical event that the user is experiencing.

2. The method of claim 1, wherein the bystander mobile device and the user mobile device are positioned such that a wireless data transfer or exchange is possible.

3. The method of claim 1, wherein the user mobile device transmits the notification to the bystander mobile device via a device-to-device network.

4. The method of claim 3, wherein the device-to-device network comprises technology that allows short-range wireless data transfer or exchange between mobile devices over short distances.

5. The method of claim 1, wherein the preset timer is a customizable preset timer.

6. The method of claim 5, wherein the customizable preset timer is adjusted by way of the user of the user mobile device prior to the manual user activation or the automatic user activation of the preset timer.

7. The method of claim 1, wherein the information indicative of the user's medical condition and the medical event that the user is experiencing is shared with a public emergency system's call coordinator and paramedics.

8. The method of claim 1, further comprising:

receiving, prior to completion of the preset timer, a manual disable command at the mobile device; and responsive to receiving the manual disable command, deactivating the preset timer.

9. The method of claim 8, further comprising:

responsive to receiving the manual disable command, causing the user mobile device to not transmit the notification to the bystander mobile device.

10. The method of claim 1, wherein in response to the at least one action of the set of actions is performed by way of the bystander on the bystander mobile device, the server sends a command to the user mobile device causing the user mobile device to play a soothing action.

11. The method of claim 10, wherein the soothing action comprises playing at least one of: music, videos, or photos, or providing a specific vibration pattern.

12. A system configured to improving response to medical events, the system comprising a user mobile device comprising:

a processor; and a memory configured to store instructions that, when executed by the processor, causes the system to carry out steps that include:

in response to a manual user activation or an automatic user activation, activating a preset timer;

in response to completion of the preset timer, causing the user mobile device to transmit a notification to a bystander mobile device so as to alert a bystander that a user of the user mobile device is experiencing a medical event and that the user may need assistance;

in response to completion of the preset timer, wherein accepting the notification by way of the bystander mobile device causes the bystander mobile device to connect to a server via a network;

upon connecting the bystander mobile device to the server, transmitting data from the server to the bystander mobile device, wherein the data comprises:

information indicative of a medical condition of the user and the medical event that the user is experiencing; and at least one action of a set of actions to be carried out on the bystander mobile device, wherein the set of actions comprises a series of actions that are customized to the user's medical condition and the medical event; and displaying, on the bystander mobile device, information corresponding to the at least one action of the set of actions, wherein the information involves a question or command to help the bystander evaluate or assist with the medical event that the user is experiencing.

13. The system of claim 12, wherein the bystander mobile device and the user mobile device are positioned such that a wireless data transfer or exchange is possible.

14. The system of claim 12, wherein the user mobile device transmits the notification to the bystander mobile device via a device-to-device network.

15. The system of claim 14, wherein the device-to-device network comprises technology that allows short-range wireless data transfer or exchange between mobile devices over short distances.

16. The system of claim 12, wherein the preset timer is a customizable preset timer.

17. The system of claim 16, wherein the customizable preset timer is adjusted by way of the user of the user mobile device prior to the manual user activation or the automatic user activation of the preset timer.

18. The system of claim 12, wherein the information indicative of the user's medical condition and the medical event that the user is experiencing is shared with a public emergency system's call coordinator and paramedics.

* * * * *